US00PP28702P3

(12) United States Plant Patent
Bradford

(10) Patent No.: US PP28,702 P3
(45) Date of Patent: Nov. 28, 2017

(54) ***FUCHSIA* PLANT NAMED 'FWUNW20-0'**

(50) Latin Name: ***Fuchsia* hybrid**
Varietal Denomination: FWUNW20-0

(71) Applicant: Marie Bradford, Dereham (GB)

(72) Inventor: Marie Bradford, Dereham (GB)

(73) Assignee: Floranova Ltd. (GB)

( * ) Notice: Subject to any disclaimer, the term of this patent is extended or adjusted under 35 U.S.C. 154(b) by 158 days.

(21) Appl. No.: 14/756,098

(22) Filed: Aug. 3, 2015

(65) Prior Publication Data

US 2017/0042076 P1 Feb. 9, 2017

(51) Int. Cl.
*A01H 5/02* (2006.01)

(52) U.S. Cl.
USPC ..... Plt./300

(58) Field of Classification Search
USPC ..... Plt./263.1, 300
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Fuchsia* cultivar named 'FWUNW20-0' is disclosed, characterized a well branched, upright mounded growth habit and strong stems. Flowers have a highly reflexed bright pink calyx, which fully exposes a white corolla. The new variety is a *Fuchsia*, typically produced as a garden or container plant.

2 Drawing Sheets

Latin name of the genus and species: *Fuchsia* hybrid.
Variety denomination: 'FWUNW20-0'.

BACKGROUND OF THE INVENTION

The new cultivar is a product of a planned breeding program. The new variety originated from a cross pollination of the seed parent, an unnamed, unpatented proprietary selection of *Fuchsia* hybrid with the pollen parent a different unnamed, unpatented *Fuchsia* hybrid. The crossing was made during July of 2010, at a research greenhouse in Norfolk, UK. 'FWUNW20-0' was discovered by the inventor, Marie Bradford at the same research greenhouse in May 2011.

Asexual reproduction of the new cultivar 'FWUNW20-0' was first performed in Norfolk, UK, at a commercial greenhouse by vegetative terminal cuttings in Summer of 2011. 'FWUNW20-0' has since produced several generations and has shown that the unique features of this cultivar are stable and reproduced true to type.

SUMMARY OF THE INVENTION

The cultivar 'FWUNW20-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FWUNW20-0'. These characteristics in combination distinguish 'FWUNW20-0' as a new and distinct *Fuchsia* cultivar:

1. Upright growth habit.
2. Distinctive clear white corolla with very faint pink veins at base.
3. Well branched plants 4. Calyx reflexed back to fully expose corolla.
5. Strong stems.

PARENT COMPARISON

Plants of the new cultivar 'FWUNW20-0' are similar to plants of the seed parent in most horticultural characteristics, however, plants of the new cultivar 'FWUNW20-0' differ in the following:

1. New variety has stronger stems.
2. Different flower color, the new variety is white, the seed parent is mainly pink.
3. Flowering begins earlier in the new variety.
4. Plant habit of the new variety is more compact and uniform, with shorter internodes than the seed parent.

Plants of the new cultivar 'FWUNW20-0' are similar to plants of the pollen parent in most horticultural characteristics, however, plants of the new cultivar 'FWUNW20-0' differ in the following:

1. The new variety flowers later.
2. New variety has a lighter colored calyx.
3. New variety is a more vigorous plant.

COMMERCIAL COMPARISON

Of the many *Fuchsia* varieties known to the inventor, the most similar is *Fuchsia* 'Marie Claire', unpatented. The new variety differs from plants of 'Marie Clair' in the following:

1. New variety flowers later.
2. New variety forms a wider plant.
3. New variety has a deeper colored calyx.
4. New variety is a much more vigorous plant.

BRIEF DESCRIPTION OF THE PHOTOGRAPHS

Figure 1:
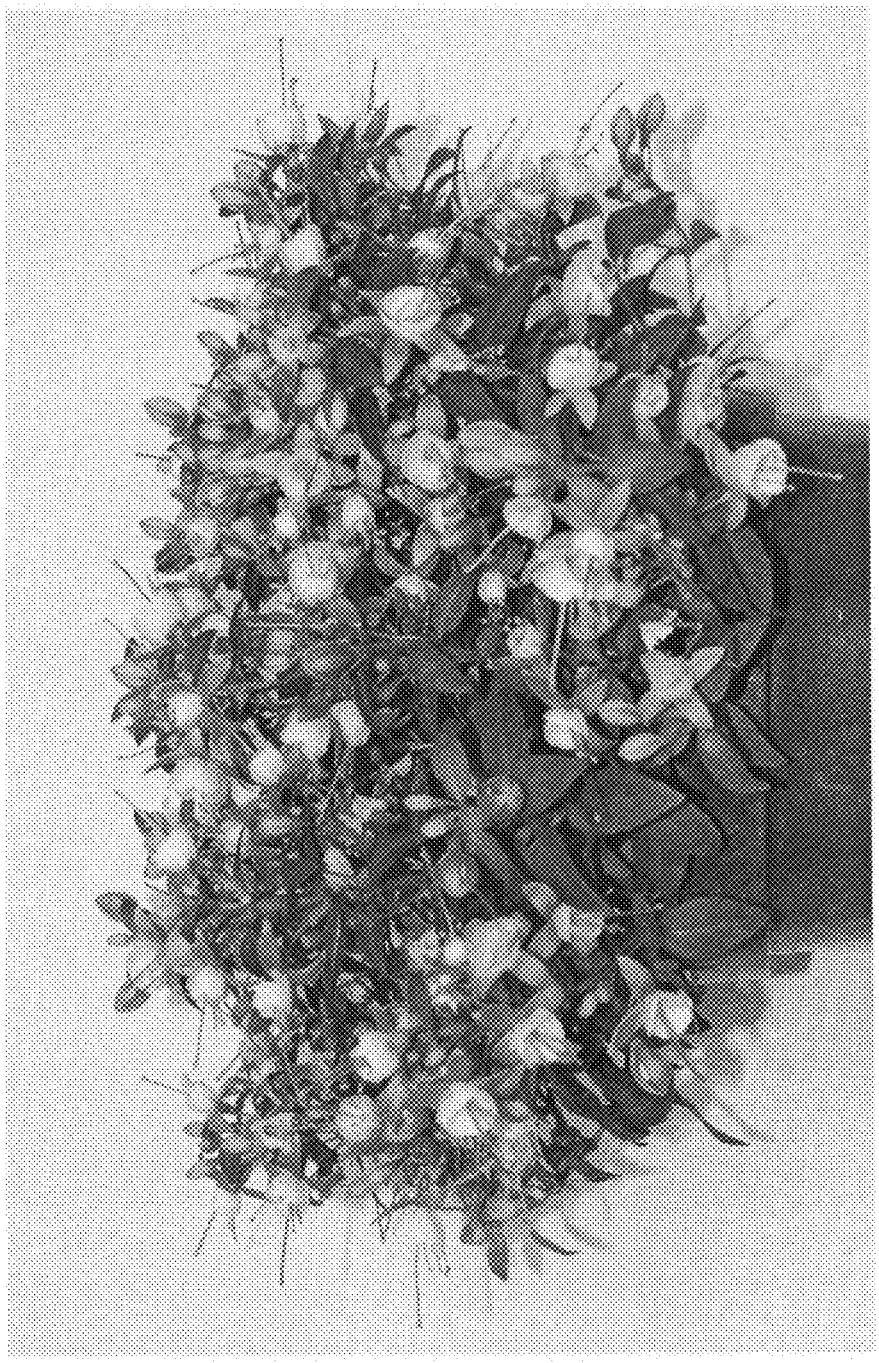

The accompanying photograph in FIG. 1 illustrates in full color a typical plant of 'FWUNW20-0' grown outdoors in Santa Paula, Calif. This plant is approximately 17 weeks old, shown in a 8 inch pot.

Figure 2:
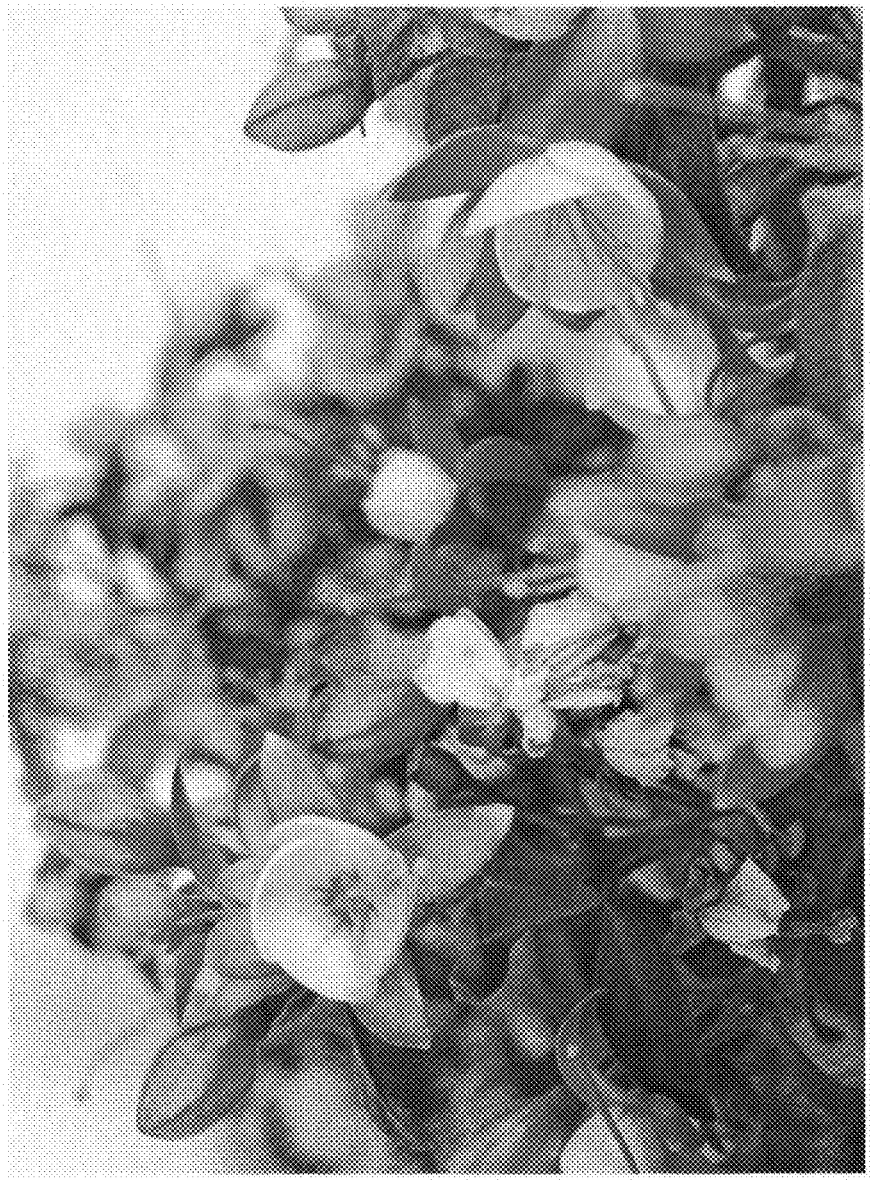

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'FWUNW20-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Fuchsia* hybrid 'FWUNW20-0'.

PROPAGATION

Propagation method: Vegetative Cuttings.

Time to initiate roots: About 2 weeks at 15° C. to 22° C.

Root description: Fine, densely fibrous.

PLANT

Age of plant described: Approximately 20 weeks from 5 rooted cuttings.

Pot size of plant described: 8 inch.

Height: Approximately 24 cm from soil line of pot to top of foliar and uppermost flowering plane.

Plant spread: Approximately 48 cm.

Growth rate: Rapid.

Growth habit: Upright.

Branching characteristics: Free branching.

Length of primary lateral branches: Average 12 to 18 cm.

Diameter of lateral branches: Approximately 0.5 cm.

Quantity of primary lateral branches: Approximately 25.

Characteristics of primary lateral branches:

- *Color.*—Near RHS yellow-Green 145A, flushed Greyed-Purple 183D.
- *Texture.*—Glabrous.
- *Strength.*—Strong, flexible.

Internode length: Average range 1.2 cm to 2.2 cm.

FOLIAGE

Leaf:

- *Arrangement.*—Opposite.
- *Quantity.*—Approximately 10 to 18 fully expanded leaves per primary lateral branch.
- *Average length.*—3.6 cm, including petiole.
- *Average width.*—1.5 cm.
- *Shape of blade.*—Ovate.
- *Apex.*—Acute.
- *Base.*—Oblique.
- *Margin.*—Shallowly and infrequently denate.
- *Texture of top surface.*—Glabrous.
- *Texture of bottom surface.*—Glabrous.
- *Aspect.*—Mostly flat.
- *Color.*—Young foliage upper side: Near RHS Yellow-Green 144B. Young foliage under side: Near RHS Green 143C. Mature foliage upper side: Near RHS Green 137A. Mature foliage under side: Near RHS Green 138A.
- *Venation.*—Type: Pinnate. Venation color upper side: Near RHS Yellow-Green 145C. Venation color under side: Near RHS Yellow-Green 145C. Attachment: Stalked.
- *Petiole.*—Length: Average 0.4 cm. Diameter: Average 0.2 cm. Texture: Glabrous. Color: Upper surface: Near RHS Yellow-Green 145C. Lower surface: Near RHS Yellow-Green 145C.

FLOWER

Natural flowering season: Spring.

Inflorescence and flower type and habit: 1 to 2 flowers emerge singly from each axil. Flowers are symmetrical and composed of a corolla surrounded by a decorative fused calyx. Flowers face outwardly or upward. Non-pendulous.

Flowers per plant: Approximately 180 fully open flowers and 50 buds on a mature plant.

Flower longevity on plant: Approximately 1 week for individual flowers.

Persistent or self-cleaning: Self-cleaning.

Flower size (petals and sepals only, not including protruding stamen and style):

- *Length.*—Approximately 2.4 cm, includes backwards reflex of sepals.
- *Width.*—Approximately 3.5 cm.

Bud:

- *Shape.*—Oblong.
- *Length.*—2.5 cm.
- *Diameter.*—1.4 cm.
- *Color.*—Near RHS Red-Purple N57A. Some streaking near Red 56D. Apex Near Green 143C.

Corolla:

Petals (measured from separation at top of tube):

- *Number.*—Average 5 to 7.
- *Length.*—Approximately 1.1 cm.
- *Width.*—Approximately 1.2 cm.
- *Shape.*—Orbicular.
- *Aspect.*—Slightly cupped upwards.
- *Margin.*—Entire.
- *Texture.*—Glabrous, all surfaces.
- *Appearance.*—Matte.
- *Apex.*—Obtuse.
- *Color.*—When opening: Upper surface: Near RHS Red 49D, vein coloration from base near Red-Purple N57B. Lower surface: Near RHS Red 49D, vein coloration from base near Red-Purple N57B. Fully opened: Upper surface: Near RHS White 155B, vein coloration from base near Red-Purple N57B. Lower surface: Near RHS White 155B, vein coloration from base near Red-Purple N57B. Fading: Upper surface: Near RHS White 155D, vein coloration from base near Red-Purple N57C. Lower surface: Near RES White 155D, vein coloration from base near Red-Purple N57C.

Calyx:

- *Form.*—Funnel form base, separating approximately 15% from base, to flare out into 4 large decorative deltoid shaped sepals. Sepals reflexed back.
- *Fused section.*—Length: Approximately 0.5 cm. Diameter: Approximately 0.5 cm.

*Unfused section*.—Length: Approximately 1.8 cm. Diameter: Approximately 0.6 cm.

*Sepal texture*.—Glabrous all surfaces.

*Appearance*.—Bright and vibrant, nearly iridescent.

*Apex*.—Acute.

*Color*.—Upper Surface: Near RHS Red 55A, but brighter. Lower Surface: Near RHS Red-Purple N57B, streaked faintly Red 56D. Small, very uppermost section of apex colored near Red 56D and occasionally Green 143C.

*Fragrance*.—None.

Peduncle:

*Length*.—Average 1.3 cm.

*Diameter*.—0.1 cm.

*Color*.—Near RHS Green 143C.

*Texture*.—Glabrous.

REPRODUCTIVE ORGANS

Stamens:

*Number* (*per flower*).—Typically 8.

*Filament length*.—Average 1.0 cm.

*Filament color*.—Near RHS Red-Purple 57C.

*Anthers*.—Shape: Globular. Length: Approximately 0.1 cm. Color: Near RHS Greyed-Purple 187A.

*Pollen*.—Amount: Not observed.

Pistils:

*Quantity per flower*.—1.

*Length*.—Approximately 4.5 cm.

*Style*.—Length: Approximately 4.0 cm. Color: Base near RHS Red-Purple 65C, upper ⅔ near Red-Purple N57A

*Stigma*.—Shape: Globular. Color: Near Red-Purple N57A. Ovary: Length: Approximately 0.4 cm. Diameter: Approximately 0.3 cm. Color: Near RHS Green 143C.

OTHER CHARACTERISTICS

Seeds and fruits: Fruit is a spherical berry colored near Green 143C. Average diameter 0.5 average height 0.6 cm. Seed production not observed.

Disease/pest resistance: Neither resistance nor susceptibility to normal diseases and pests of *Fuchsia* has been observed.

Temperature tolerance: Tolerates temperatures from approximately −1° C. to 38° C.

Drought tolerance: No tolerance for drought.

What is claimed is:

1. A new and distinct cultivar of *Fuchsia* plant named 'FWUNW20-0' as herein illustrated and described.

* * * * *